(12) United States Patent
Sreekumar

(10) Patent No.: US 10,024,835 B2
(45) Date of Patent: Jul. 17, 2018

(54) APPARATUS FOR MEASURING A HIGHER CONCENTRATION OF FLUORESCENT MATERIALS IN A LIQUID

(71) Applicant: Advanced Sensors Limited, Carrickfergus (GB)

(72) Inventor: Jeyan Sreekumar, Newtownabbey (GB)

(73) Assignee: Advanced Sensors Limited, Carrickfergus (GB)

( * ) Notice: Subject to any disclaimer, the term of this patent is extended or adjusted under 35 U.S.C. 154(b) by 0 days.

(21) Appl. No.: 14/812,026

(22) Filed: Jul. 29, 2015

(65) Prior Publication Data
US 2017/0030884 A1    Feb. 2, 2017

(51) Int. Cl.
  *G01N 21/64* (2006.01)
  *G01N 21/85* (2006.01)
  *G01N 33/18* (2006.01)
  *G01N 33/28* (2006.01)
  *G01N 29/00* (2006.01)

(52) U.S. Cl.
  CPC ....... *G01N 33/2823* (2013.01); *G01N 21/643* (2013.01); *G01N 21/645* (2013.01); *G01N 29/00* (2013.01); *G01N 2021/6484* (2013.01)

(58) Field of Classification Search
  CPC .. G01N 21/645; G01N 21/64; G01N 21/8507; G01N 33/1833; G01N 33/2823; G01N 2021/6484
  USPC ....... 250/458.1, 461.1, 269.1, 301, 574, 573
  See application file for complete search history.

(56) References Cited

U.S. PATENT DOCUMENTS

| | | | | |
|---|---|---|---|---|
| 4,034,219 A | * | 7/1977 | Louden | G01N 33/1833 250/301 |
| 4,105,334 A | * | 8/1978 | Halko | G01N 21/8507 250/574 |
| 4,577,110 A | * | 3/1986 | MacBride | G01N 21/645 250/461.2 |
| 4,797,550 A | * | 1/1989 | Nelson | B03B 13/02 209/166 |
| 4,895,156 A | * | 1/1990 | Schulze | A61B 5/1459 250/458.1 |
| 4,977,319 A | * | 12/1990 | Supernaw | G01N 33/241 250/255 |
| 4,990,773 A | * | 2/1991 | Supernaw | G01N 21/64 250/255 |
| 5,151,869 A | * | 9/1992 | Alcala | G01N 21/6408 250/458.1 |
| 5,341,805 A | * | 8/1994 | Stavridi | A61B 5/0071 356/317 |

(Continued)

*Primary Examiner* — David Porta
*Assistant Examiner* — Blake Riddick
(74) *Attorney, Agent, or Firm* — Snyder, Clark, Lesch & Chung, LLP

(57) ABSTRACT

An apparatus for measuring oil in water for larger parts per million (ppm) of light-to-medium weight crude oils shown. The excitation signal and the fluorescent light being detected are provided and received through a single channel within the ultrasonic transducer. The target area for measuring the ppm's of oil in water is located just inside of the measurement window to prevent interference by turbidity or other oil droplets within the fluid stream. The angle between the excitation signal and the fluorescent light as transmitted and received from the single channel is very small.

6 Claims, 6 Drawing Sheets

(56) References Cited

U.S. PATENT DOCUMENTS

| | | | | |
|---|---|---|---|---|
| 5,370,119 A | * | 12/1994 | Mordon | A61B 5/0071 600/317 |
| 5,381,002 A | * | 1/1995 | Morrow | G01N 33/1833 250/301 |
| 5,656,810 A | * | 8/1997 | Alfano | G01N 21/64 250/255 |
| 5,686,724 A | * | 11/1997 | Spilker | E21B 49/005 250/255 |
| 5,740,291 A | * | 4/1998 | De Lasa | G01P 5/26 250/227.11 |
| 5,780,850 A | * | 7/1998 | DeLaune | E21B 49/005 250/255 |
| 6,324,900 B1 | * | 12/2001 | Bruno | B08B 7/028 356/928 |
| 6,407,383 B1 | * | 6/2002 | Byatt | G01N 33/1833 250/301 |
| 7,099,012 B1 | * | 8/2006 | Crawford | G01N 21/645 250/458.1 |
| 7,657,133 B2 | * | 2/2010 | Hecht | B82Y 20/00 385/12 |
| 7,935,938 B2 | | 5/2011 | Thalbeth et al. | |
| 2005/0122225 A1 | * | 6/2005 | Kram | G01M 3/38 340/605 |
| 2007/0210262 A1 | * | 9/2007 | Pearlman | G01J 3/02 250/461.1 |
| 2008/0173805 A1 | * | 7/2008 | Indo | E21B 47/102 250/269.1 |
| 2008/0203332 A1 | * | 8/2008 | McStay | G01N 21/8507 250/553 |
| 2009/0032733 A1 | * | 2/2009 | Thabeth | G01N 21/15 250/458.1 |
| 2009/0310127 A1 | * | 12/2009 | Parks, II | G01N 21/6402 356/70 |
| 2010/0163718 A1 | * | 7/2010 | Schaefer | E21B 47/10 250/269.1 |
| 2011/0105869 A1 | * | 5/2011 | Wilson | A61B 5/14539 600/323 |
| 2016/0195508 A1 | * | 7/2016 | Al-Hajji | G01N 33/2823 250/301 |

* cited by examiner

APPARATUS FOR MEASURING A HIGHER CONCENTRATION OF FLUORESCENT MATERIALS IN A LIQUID

CROSS REFERENCE TO RELATED APPLICATIONS

This is an improvement over U.S. Pat. No. 7,935,938, issued on May 3, 2011, entitled "Apparatus for Measuring Fluorescent Material in a Liquid," which patent is hereby incorporated by reference.

BACKGROUND OF THE INVENTION

Technical Field

This invention relates to an apparatus for measuring fluorescent material in a liquid and, more particularly, greater concentrations of fluorescent materials in a liquid than could previously be measured.

Description of the Prior Art

With the world's dependency on oil, more oil is being processed in oil refineries and shipped by pipelines than ever before. Many of the pipes (a) leading from/to oil production or (b) within refining operations require measuring the amount of oil that may be in a liquid (mainly water) flowing in the pipes. To aid in this process, in-line measuring apparatuses are commonly used to measure the amount of oil that is present in the pipe.

When subject to certain lights, oil has a natural fluorescence. The common way of determining the amount of oil presence is to measure the amount of fluorescence that can be processed. The measuring of the amount of oil present is commonly done by a fluorometer. A typical in-line fluorometer has an excitation light source which transmits the light onto the sample to a measurement region through a measurement window. When the oil in sample absorbs the light, it fluoresces. The resultant fluorescence light is transmitted back through the measurement window and is received by the fluorescence detector. By measuring the amount of fluorescent light, the amount of oil present in the water can be determined. However, in the prior systems, the measurement was accurate only up to a certain concentration of oil in water. The incorporated reference would only detect oil in water up to approximately 1,000 parts per million (hereinafter "ppm") before measurements started losing accuracy.

Applicant has discovered modifications that can be made to the incorporated reference to greatly improve the accuracy of measurements of oil-in-water in ppm at higher concentrations, which significantly increases accuracy of measurements from 1,000 ppm to 100,000 ppm (10%) of oil in water.

BRIEF SUMMARY OF THE INVENTION

It is an object of the present invention to extend the range of measurements of the incorporated reference to higher ppm of oil in water.

It is another object of the present invention to modify the incorporated reference to use a single channel through which an excitation signal is transmitted and a fluorescent signal is received from a measurement chamber.

It is yet another object of the present invention to utilize a simple optical fiber for (1) transmitting the excitation signal and (2) receiving the fluorescent signal from the oil in water to determine in ppm a concentration of oil therein.

It is a further object of the present invention to modify the incorporated reference to use a laser as an excitation signal and spectrometer as a detector of the fluorescent signal.

It is yet another object of the present invention to modify the incorporated reference so that the target point for the fluorescent is close to the inner face of the measurement window.

It is yet another object of the present invention to modify the incorporated reference wherein the transmitted signal and the fluorescent signal are arranged such that the line of sight of the excitation signal and a fluorescent signal lie in a common plane which is not perpendicular with the inner surface of the measurement window.

It is still another object of the present invention wherein the line of sight of the excitation signal is at an obtuse angle with the line sight to the fluorescent signal.

It is another object of the present invention to have a measurement chamber with a measurement window with a single channel through which an excitation signal is transmitted and a fluorescent signal is detected using bifurcated fiber optics and an ultrasonic transducer for keeping the measurement window clean.

It is another object of the present invention to modify the incorporated reference so that lines of sight of (1) an excitation signal and (2) another light guide intersect in a measurement chamber to define a target region from which fluorescent light may be detected, said target region being located within the measurement chamber substantially at the inner face.

BRIEF DESCRIPTION OF THE DRAWINGS

FIG. 4(*b*) are measurements of the fluorescent material at different ppm in a system incorporating the current improvements over the incorporated reference.

DESCRIPTION OF THE PREFERRED EMBODIMENT

Figure 1:
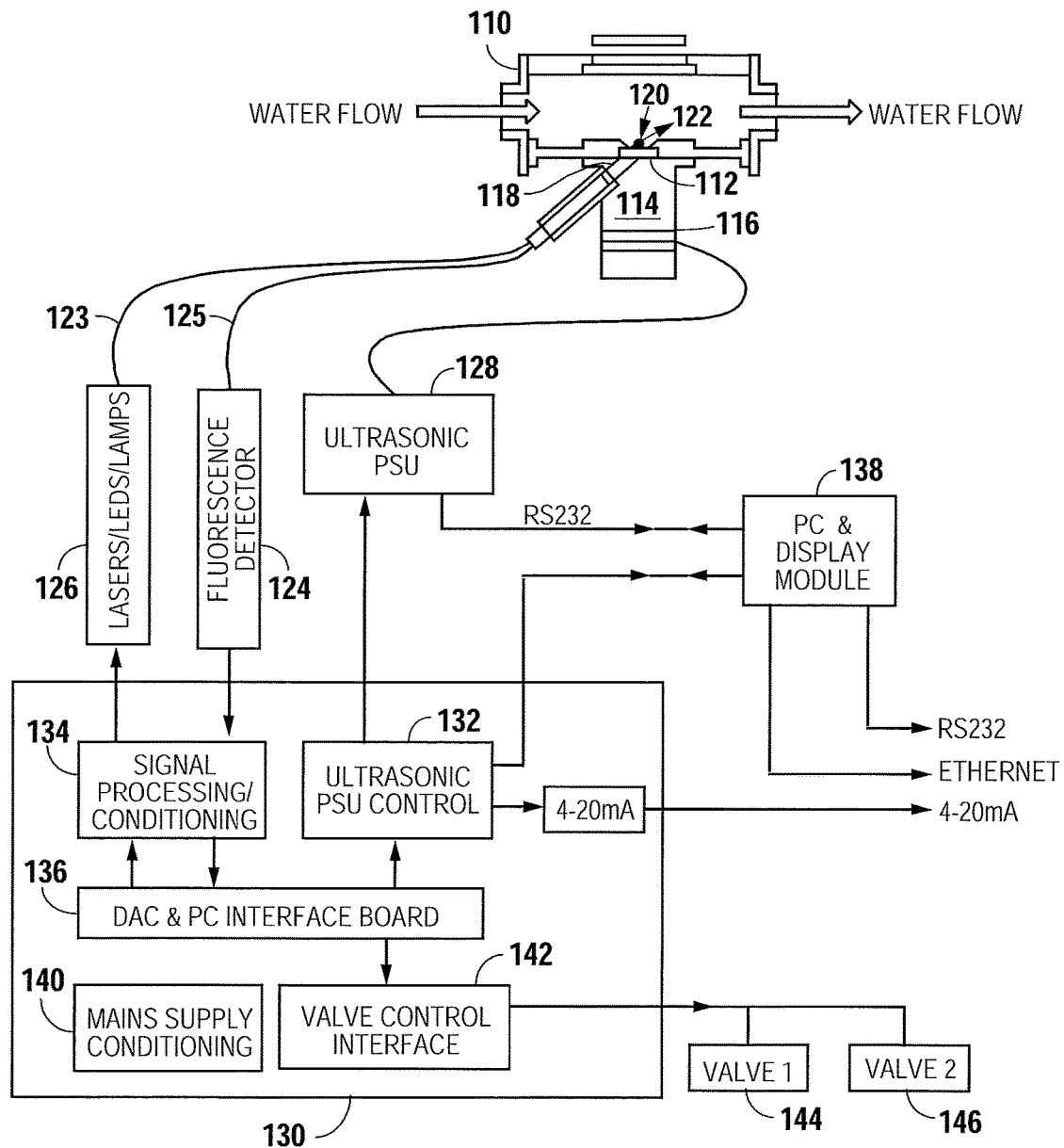
FIG. 1 is a schematic view of an apparatus embodying the present invention.

Having previously incorporated by reference U.S. Pat. No. 7,935,938, over which the present invention is an improvement, all reference numerals given herein below will start with the number 110 or higher so that none of the reference numerals will conflict with the reference numerals of the incorporated reference.

Referring to FIG. 1 of the present invention, a measurement chamber 110 is shown with water flowing there through. A measurement window 112 is provided on one side of the measurement chamber 110. In contact with the measurement window 112 is a coupling mass 114, with piezoelectric transducers 116 being located in the coupling mass 114 but away from the measurement window 112.

Connecting through the coupling mass 114 to the measurement window 112 is a single channel 118. Through the single channel 118, an excitation signal 122 is transmitted and fluorescent light 120 is collected or received using the light guides 123 and 125, respectively. The excitation signal 122 can be lasers, light emitting diodes or lamps 126. What is required is that the excitation signal 122 cause oil particles contained in the water flow to fluoresce so that the fluorescent light 120 can be detected by fluorescent detector 124. The excitation signal 122 is provided by an excitation source 126. The piezoelectric transducers 116 are energized by ultrasonic power supply 128.

The apparatus as shown in FIG. 1 has a master circuit board 130. While the composition and configuration of the circuitry may vary, an illustrated example of the circuitry includes an ultrasonic power supply control 132 for the ultrasonic power supply 128. A signal processing/conditioning unit 134 prepares a signal for the excitation source 126 (i.e., lasers/LEDs/lamps) and conditions the fluorescent light signal received from the fluorescent detector 124.

An interface unit 136 provides interfacing between the signal processing/conditioning unit 134, ultrasonic power supply control 132 and the computer 138. The computer 138 will have an internal display module, plus the computer 138 can either (1) connect to an RS232 connector or (2) to the Ethernet. The computer 138 will be appropriately programmed to operate the apparatus shown in FIG. 1. The computer 138 may be at the site with the rest of the apparatus shown in FIG. 1, or remotely located.

A power supply conditioning unit 140 is provided to operate the circuitry shown in FIG. 1.

Fluid flow through the measurement chamber 110 may be controlled by valve control interface 142, which controls operation of valve 144 or valve 146. Valve 144 may be located at one end of the measurement chamber 110, and valve 146 may be located at the opposite end thereof so that a liquid sample may be captured within measurement chamber 110 if desired.

Figure 2:
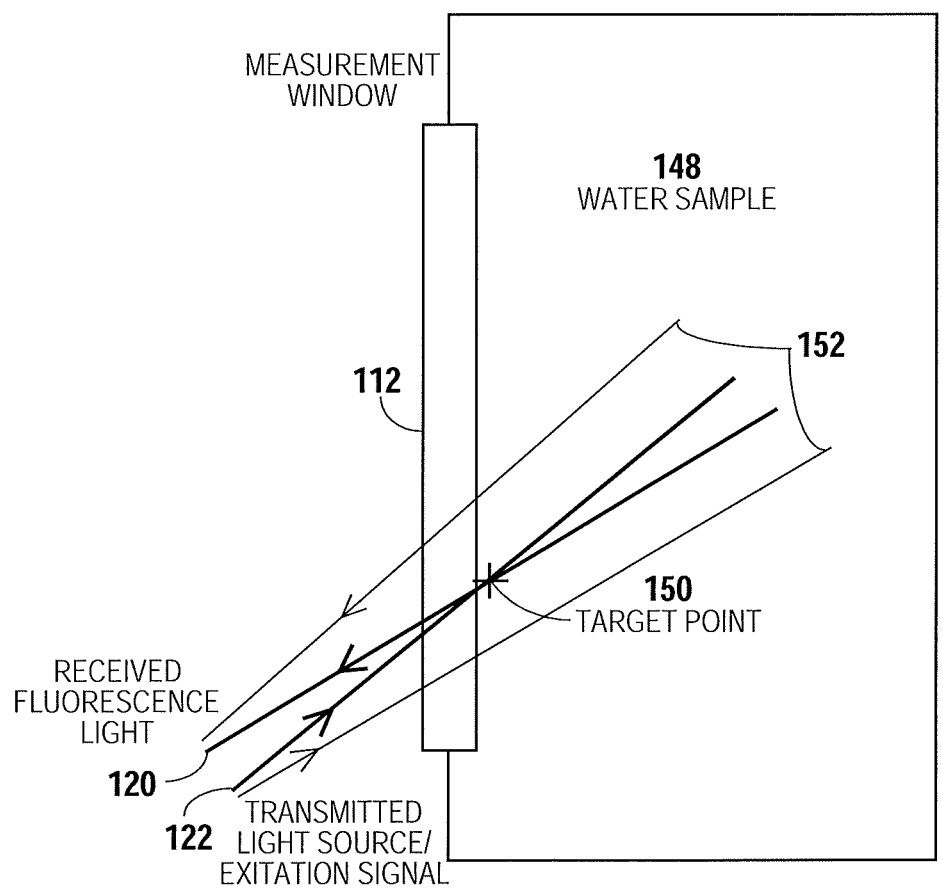
FIG. 2 is a pictorial view of a measurement chamber from the apparatus as shown in FIG. 1.

Referring now to FIG. 2, a water sample 148 is shown, which water sample 148 could be inside of measurement chamber 110. A measurement window 112 is provided through which access is obtained to the water sample 148. The excitation signal 122 is transmitted through the measurement window 112 to a target point 150, which target point 150 is just inside the measurement window 112. Any oil contained in the water sample 148 at target point 150 will create a fluorescent light 120 that is received back through the measurement window 112. As can be seen in FIG. 2, the angle between the excitation signal 122 and the fluorescent light 120 is very small. The excitation signal 122 and the fluorescent light 120 are very close together and are within a narrow envelope 152.

Figure 3:
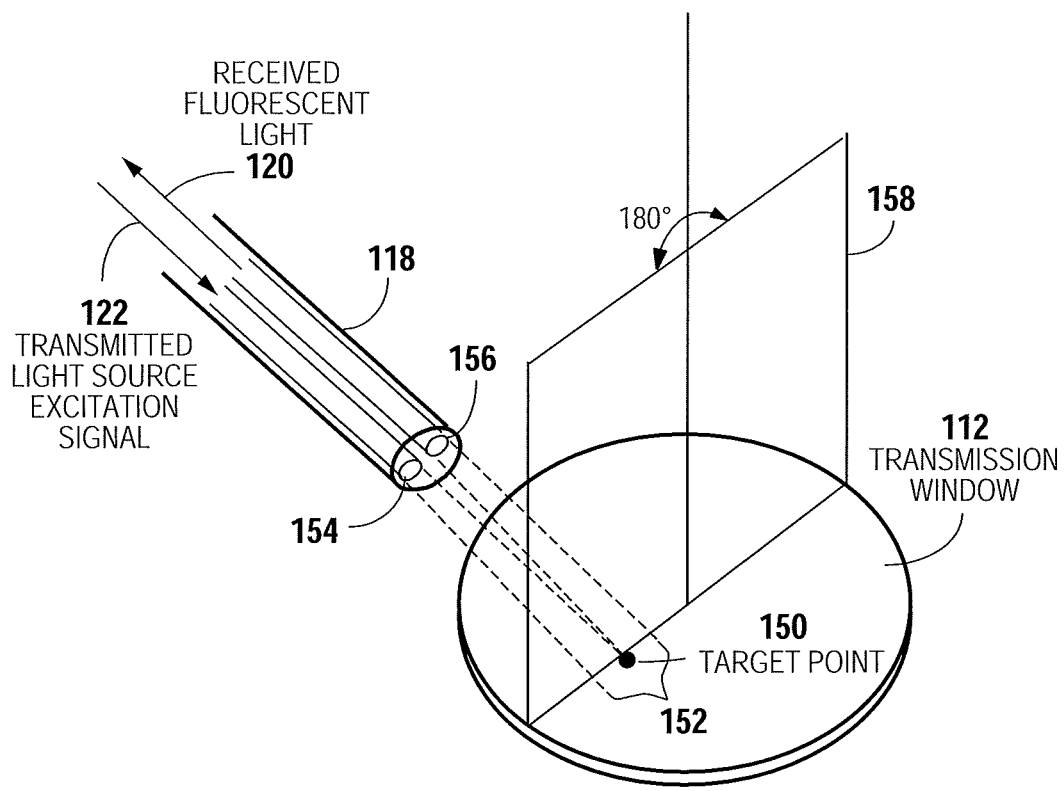
FIG. 3 is a schematic view of a preferred spatial relationship between a transmitted excitation light and a received fluorescent signal from the apparatus shown in FIG. 1.

Referring to FIG. 3, a further pictorial illustration of how the excitation signal 122 and the fluorescent light 120 are transmitted and received is illustrated. The single channel 118 (a) provides the excitation signal 122 and (b) receives the fluorescent light 120. Inside of the single channel 118 are fiber optic ends 154 and 156. The fiber optic ends 154 may be a single fiber optic that is split on the end thereof, are two separate strands of fiber optics contained in single channel 118. In either event, the fiber optic ends 154 and 156 are in close proximity to each other. The angle at which the excitation signal 122 strikes the transmission window 112 is at a substantial angle to the perpendicular plane 158 of the transmission window 112. Likewise, the angle at which the fluorescent light 120 is received from the target point 150 is also at a substantial angle with respect to the perpendicular plane 158.

Using the invention as shown in the incorporated reference, it is difficult to make measurements of oil-in-water for both conventional light and medium crude oils if the ppm's exceed the 1,000 ppm range. This is demonstrated in FIG. 4A attached hereto where measurements are made of a crude oil for parts per million (ppm) varying from 0 to 5,000. As can be seen in FIG. 4A if the ppm's exceed 1,000, the relationship becomes non-linear and concentration quenching occurs between concentrations 1,000 ppm and 5,000 ppm. FIG. 4A gives the light intensity plotted versus the wavelength for a crude oil at varying ppm's. The light intensity plotted versus ppm is shown in the upper right plot.

Figure 4B:
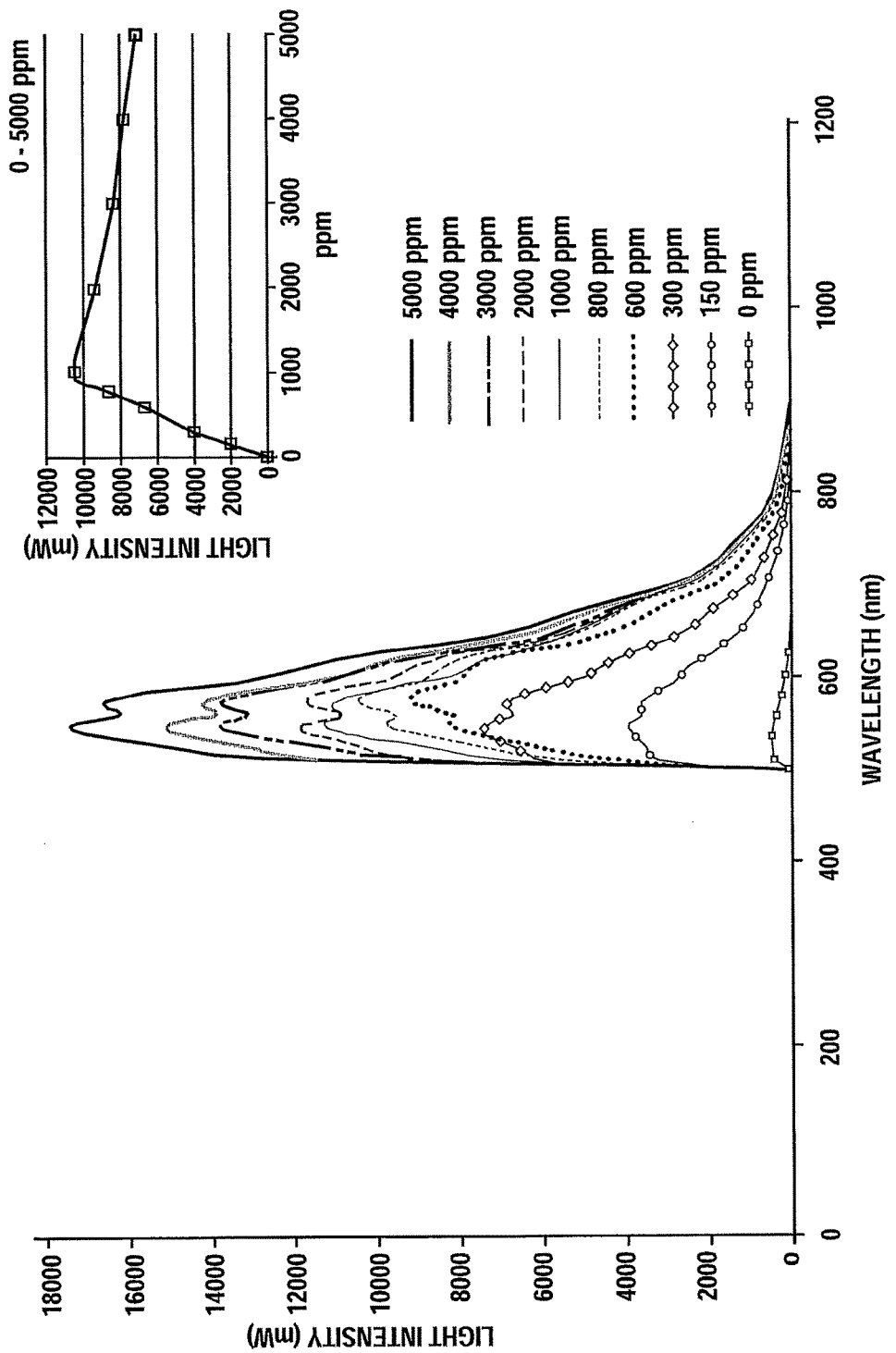
FIG. 4(*a*) are measurements of fluorescent materials at different ppm in the incorporated reference of U.S. Pat. No. 7,935,938.
Figure 4B:
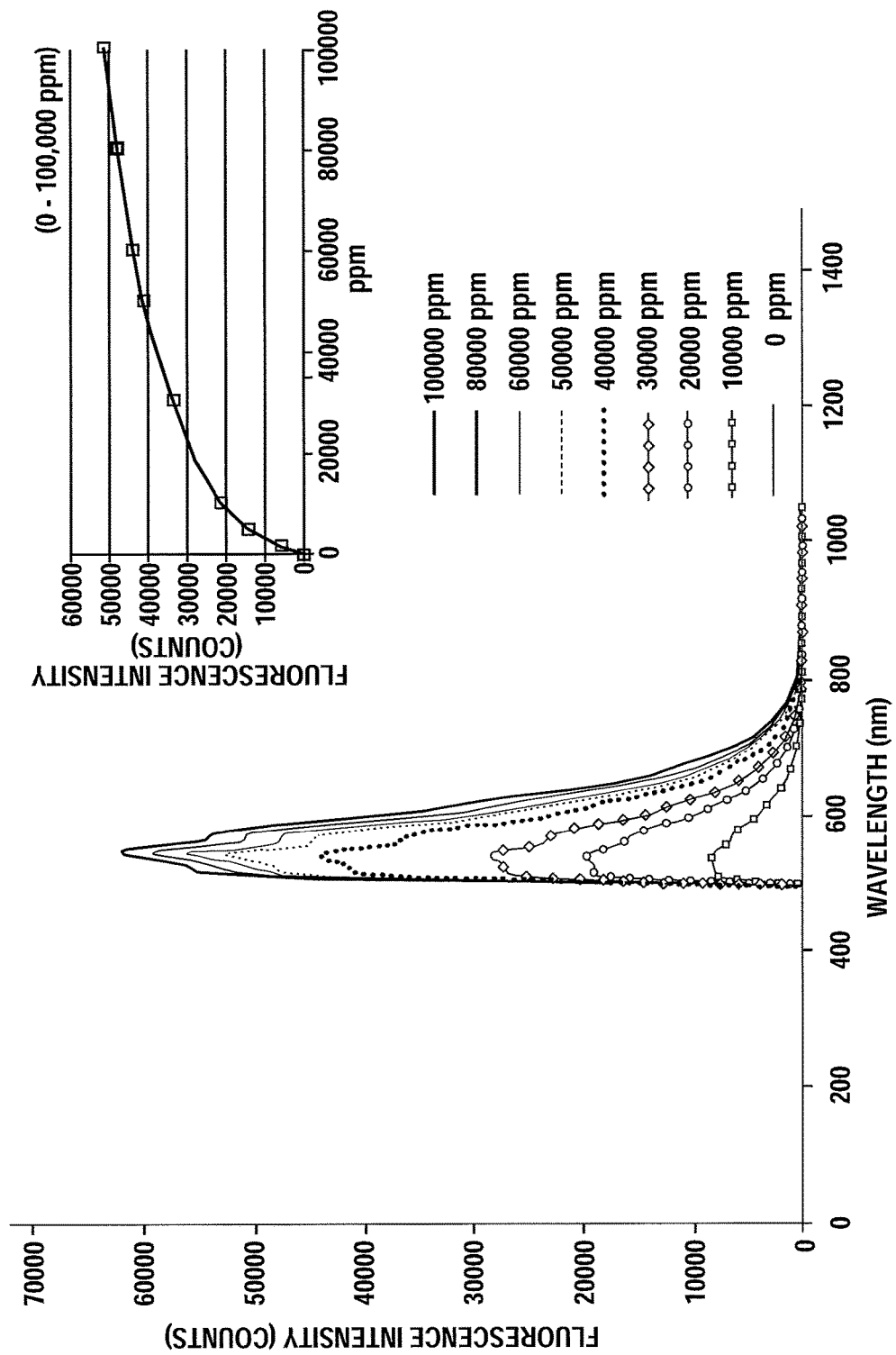

Modifying the prior invention incorporated by reference to utilize the features shown herein for crude oil is again run, but at higher ppm's range of 0 to 100,000 (see FIG. 4B). As can be seen in the upper right chart of FIG. 4B, the light intensity continues as a linear function of the ppm's up to approximately 100,000 ppm. This illustrates how the incorporated invention once modified as illustrated herein increases the sensitivity of the incorporated reference at higher ppm' of light-to-medium weight crude oil.

Different oils were examined and the results obtained were similar to the discussed results.

Figure 5:
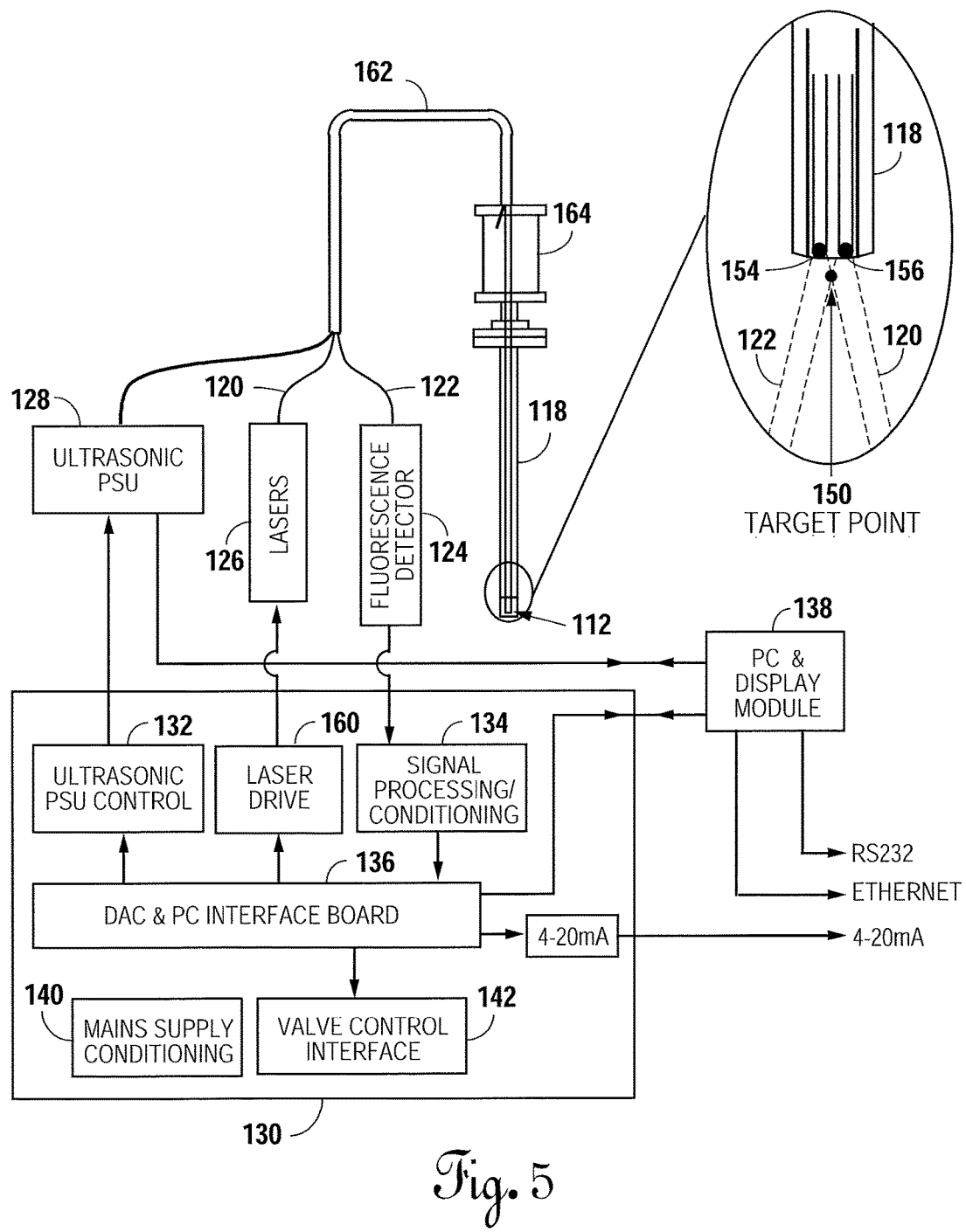
FIG. 5 is a modified schematic from FIG. 1 further illustrating changes from the incorporated reference.

Referring to FIG. 5, the apparatus as shown in FIG. 1 is given in further detail with the single channel 118 being illustrated in an enlarged view. In this embodiment as shown in FIG. 5, the excitation source 112 of lasers has a laser drive 160.

A single cable 162 connects to the ultrasonic transducer 164, which then has a single channel 118 pointing at the target point 150 through the measurement window 112. Inside of the single channel 118 are the fiber optic ends 154 and 156. The fiber optic ends 154 and 156 may be a single fiber optic split on each end thereof, or two separate fiber optic strands. In either event, fiber optic ends 154 and 156 are located adjacent to each other. Therefore, the angle between the excitation signal 122 and the fluorescent light 120 is very small; however, that angle is enlarged in FIG. 5 for purposes of illustration.

What I claim is:

1. An apparatus for measuring amounts of light-to-medium crude oil in water, the apparatus comprising:
    a measurement chamber comprising a measurement window, wherein an excitation signal having wavelength greater than 400 nm is transmitted through the measurement window toward a target point to measure a concentration of the light-to-medium crude oil in the water, wherein fluorescent light is detected from the target point through the measurement window, and wherein paths travelled by the excitation signal and the fluorescent light lie in a common plane that is not perpendicular with an inner surface of the measurement window;
    a light source for generating the excitation signal;
    a detector for receiving the fluorescent light;
    an ultrasonic transducer comprising a transducer mass coupled to the measurement chamber and the measurement window;
    a source of power for the apparatus;
    controls including an ultrasonic transducer control for the ultrasonic transducer and a signal processing/conditioning unit for the fluorescent light, wherein the controls determine, from the fluorescent light, an amount of the light-to-medium crude oil in the water at the target point;
    a single channel through the ultrasonic transducer terminating adjacent an outside surface of the measurement window; and optics within the single channel, the optics including a transmitting fiber optic end for delivering the excitation signal to the target point and a receiving fiber optic end for receiving the fluorescent light from the target point, wherein the transmitting fiber optic end is parallel and adjacent to the receiving fiber optic end.

2. The apparatus of claim 1, wherein the target point is located adjacent the measurement window.

3. The apparatus of claim 2, wherein an angle between the excitation signal and the fluorescent light is less than 5 degrees.

4. The apparatus of claim 3, wherein the optics are a single fiber optic cable split on each end.

5. The apparatus of claim 3, wherein a striking angle at which the excitation signal hits the measurement window is obtuse.

6. The apparatus of claim 1, wherein an angle at which the fluorescent light is received through the measurement window is obtuse.

\* \* \* \* \*